United States Patent
Freund et al.

(10) Patent No.: US 11,123,029 B2
(45) Date of Patent: Sep. 21, 2021

(54) METHOD FOR PRODUCING A GRID-LIKE BEAM COLLIMATOR, GRID-LIKE BEAM COLLIMATOR COMPRISING A GRID STRUCTURE HAVING METAL PARTICLES AND A CURED STIFFENING MATERIAL, RADIATION DETECTOR, AND MEDICAL IMAGING DEVICE

(71) Applicant: Siemens Healthcare GmbH, Erlangen (DE)

(72) Inventors: Andreas Freund, Heroldsbach (DE); Harald Geyer, Bubenreuth (DE); Stefan Wirth, Erlangen (DE); Guido Stiebritz, Jena (DE); Thomas Studnitzky, Dresden (DE); Kay Reuter, Dresden (DE); Francois Dary, Needham, MA (US); Mike Stawovy, Cleveland Heights, OH (US)

(73) Assignee: SIEMENS HEALTHCARE GMBH, Erlangen (DE)

(*) Notice: Subject to any disclaimer, the term of this patent is extended or adjusted under 35 U.S.C. 154(b) by 16 days.

(21) Appl. No.: 16/445,928

(22) Filed: Jun. 19, 2019

(65) Prior Publication Data
US 2019/0388043 A1 Dec. 26, 2019

(30) Foreign Application Priority Data
Jun. 20, 2018 (EP) .................................... 18178847

(51) Int. Cl.
*A61B 6/00* (2006.01)
*A61B 6/03* (2006.01)
(Continued)

(52) U.S. Cl.
CPC ............ *A61B 6/4291* (2013.01); *A61B 6/032* (2013.01); *A61B 6/42* (2013.01); *A61B 6/4208* (2013.01);
(Continued)

(58) Field of Classification Search
CPC .......... A61B 6/032; A61B 6/035; A61B 6/06; A61B 6/42; A61B 6/4208; A61B 6/4233;
(Continued)

(56) References Cited

U.S. PATENT DOCUMENTS 5,606,589 A * 2/1997 Pellegrino .............. A61B 6/502
378/147
5,956,382 A * 9/1999 Wiener-Avnear ......... G01T 1/20
378/98.8
(Continued)

FOREIGN PATENT DOCUMENTS

DE        10241423 A1   3/2004
DE    102005044650 A1   3/2007
(Continued)

OTHER PUBLICATIONS

Extended European Search Report from EP Appln. No. 19180891.4 dated Oct. 14, 2019.
(Continued)

*Primary Examiner* — Allen C. Ho
(74) *Attorney, Agent, or Firm* — Harness Dickey & Pierce P.L.C.

(57) ABSTRACT

A method is for producing a grid-like beam collimator. In an embodiment, the method includes printing a suspension, including a binder and metal particles, in several stacked layers to build a layer stack with a grid structure including a number of crossing webs, and removing the binder from the layer stack. In an embodiment, the printing includes applying a curable liquid stiffening material at least on a
(Continued)

surface of the grid structure, and curing the curable liquid stiffening material after the applying.

21 Claims, 4 Drawing Sheets (51) Int. Cl.
  *G21K 1/02* (2006.01)
  *B33Y 10/00* (2015.01)
  *B33Y 70/00* (2020.01)
  *B33Y 80/00* (2015.01)
  *B29C 64/165* (2017.01)
  *B22F 10/10* (2021.01)
  *B29K 505/00* (2006.01)
  *B29L 11/00* (2006.01)

(52) U.S. Cl.
  CPC ............. *A61B 6/4233* (2013.01); *A61B 6/44* (2013.01); *A61B 6/4429* (2013.01); *A61B 6/4435* (2013.01); *A61B 6/4441* (2013.01); *A61B 6/4447* (2013.01); *B22F 10/10* (2021.01); *B29C 64/165* (2017.08); *B33Y 10/00* (2014.12); *B33Y 70/00* (2014.12); *B33Y 80/00* (2014.12); *G21K 1/02* (2013.01); *G21K 1/025* (2013.01); *B29K 2505/00* (2013.01); *B29L 2011/00* (2013.01)

(58) Field of Classification Search
  CPC ....... A61B 6/4291; A61B 6/44; A61B 6/4429; A61B 6/4435; A61B 6/4441; A61B 6/4447; G21K 1/02; G21K 1/025
  USPC ............ 378/7, 19, 98.8, 147, 149, 154, 155; 250/370.09
  See application file for complete search history.

(56) References Cited

U.S. PATENT DOCUMENTS

| | | | |
|---|---|---|---|
| 5,989,476 A | 11/1999 | Lockard et al. | |
| 6,470,072 B1* | 10/2002 | Johnson | G21K 1/025 378/150 |
| 6,594,878 B2* | 7/2003 | Kohda | G21K 1/025 156/224 |
| 6,951,628 B2 | 10/2005 | Eidam et al. | |
| 6,987,836 B2* | 1/2006 | Tang | G21K 1/025 378/147 |
| 7,141,812 B2* | 11/2006 | Appleby | G21K 1/02 250/505.1 |
| 7,149,283 B2* | 12/2006 | Hoheisel | G21K 1/025 378/149 |
| 7,362,849 B2 | 4/2008 | Short et al. | |
| 7,410,606 B2* | 8/2008 | Appleby | B29C 33/12 264/219 |
| 7,462,852 B2* | 12/2008 | Appleby | B29C 39/021 250/505.1 |
| 7,518,136 B2* | 4/2009 | Appleby | B29C 39/021 250/505.1 |
| 7,785,098 B1* | 8/2010 | Appleby | G21K 1/02 425/470 |
| 7,922,923 B2* | 4/2011 | Tang | G21K 1/025 216/36 |
| 8,314,412 B2* | 11/2012 | Vogtmeier | G21K 1/025 250/505.1 |
| 8,385,499 B2* | 2/2013 | Wu | A61B 6/032 378/19 |
| 8,515,013 B2* | 8/2013 | Vogtmeier | B22F 7/002 378/154 |
| 9,047,999 B2* | 6/2015 | Beck | G21K 1/025 |
| 9,583,228 B2* | 2/2017 | Eichenseer | G21K 1/10 |
| 9,966,158 B2* | 5/2018 | Reitz | G21K 1/025 |
| 10,090,072 B2* | 10/2018 | Deych | B29C 70/58 |
| 10,274,610 B2* | 4/2019 | Nelson | A61B 6/4233 |
| 10,408,947 B2* | 9/2019 | Beacham | G01T 1/2002 |
| 10,835,189 B2* | 11/2020 | Clark | G21K 1/02 |
| 2004/0131158 A1 | 7/2004 | Hoheisel et al. | |
| 2007/0064878 A1 | 3/2007 | Heismann | |
| 2008/0023636 A1 | 1/2008 | Chowdhury et al. | |
| 2010/0276829 A1 | 11/2010 | Yang et al. | |
| 2011/0019801 A1 | 1/2011 | Eichenseer et al. | |
| 2015/0078534 A1 | 3/2015 | Eichenseer et al. | |

FOREIGN PATENT DOCUMENTS

| | | |
|---|---|---|
| DE | 102010011581 A1 | 2/2011 |
| DE | 102012206546 A1 | 10/2013 |

OTHER PUBLICATIONS

Maeder, Thomas et al. "Formulation and processing of screen-printing vehicles for sacrificial layers on thick-film and LTCC substrates," XXXII International Conference of IMAPS Poland Chapter (2008).

* cited by examiner

METHOD FOR PRODUCING A GRID-LIKE BEAM COLLIMATOR, GRID-LIKE BEAM COLLIMATOR COMPRISING A GRID STRUCTURE HAVING METAL PARTICLES AND A CURED STIFFENING MATERIAL, RADIATION DETECTOR, AND MEDICAL IMAGING DEVICE

PRIORITY STATEMENT

The present application hereby claims priority under 35 U.S.C. § 119 to European patent application number EP 18178847.2 filed Jun. 20, 2018, the entire contents of which are hereby incorporated herein by reference.

FIELD

At least one embodiment of the invention generally relates to a method for producing a grid-like beam collimator by printing, wherein a suspension comprising a binder and metal particles is printed in several stacked layers for building a layer stack with a grid structure with a number of crossing webs.

BACKGROUND

Grid-like beam collimators, also referred to as scattered radiation grids, are used in X-ray systems like CT systems (CT=computed tomography) or angiography systems to absorb scattered radiation. Usually stacks of thin metal plates bonded in a support mechanism were used for building such a collimator. The thin metal plates made of tungsten or molybdenum where inserted and glued in a plastic carrier. This collimators allow the suppression of scattered radiation in the phi direction, in other words in the gantry rotation direction of a CT system. As it is known, a scattered beam correction is much more effective with the collimator acting in the phi direction and the z direction than with a simple phi collimator, particularly in dual source systems, a new type of collimators was developed. Among these collimators printed collimators are known, see for example DE 10 2012 206 546 A1. A suspension or paste comprising a carrier medium with metal particles is screen printed in several layers to form a layer stack. As metal particles tungsten, molybdenum, tantal or copper are used. When printing layer after layer a three dimensional grid or web structure is built. By changing the sieve to smaller openings, it is also possible to adapt the webs of the grid to a focus, so that the openings or channels have a frustum form.

After printing the layer stack or web it is necessary to remove the binder and to sinter the web structure for hardening it. During this sintering process the web structure is heated, so that the metal particle are firmly sintered together making the collimator or anti scatter grid stable.

This sintering process bears the problem, that the printed web structure or stack shrinks in an uncontrolled manner, while this shrinking is not equal in all parts of the web structure, so that it is not possible to predict the final thickness of the webs of the grid and the respective position at the sintered grid structure. A process stability is hard to achieve, the performance of the produced collimator or grid differs from one collimator to the other.

SUMMARY

At least one embodiment of the invention provides for a method for producing a grid-like beam collimator which allows more precise production of a printed collimator.

A problem is solved by at least one embodiment of the method for producing a grid-like beam collimator, wherein the binder is removed from the layer stack, whereupon a curable liquid stiffening material is applied at least on the surface of the grid structure, which a stiffening substance or a stiffening material is cured after the application.

At least one embodiment of the inventive method allows the production of a grid-like beam collimator by printing a suspension or paste through a sieve for building a layer stack without any shrinking problems due to a sintering heat treatment. According to at least one embodiment of the inventive method, the grid structure is printed in the first step. Afterwards the binder is removed from the layer stack, which binder is part of the suspension. Furthermore, liquid stiffening substance or a stiffening material is applied to the grid structure, at least on the surface of the grid structure for covering the same. The application can be done in separate ways to which reference is made afterwards. The stiffening substance or a stiffening material is curable, as it can be transferred from its liquid state, which has it while it is applied, to a solidified state after curing. In this solidified state the stiffening substance or a stiffening material stiffens and stables the layer stack respectively the grid structure, so that it is hard enough to be further processed.

At least one embodiment is furthermore directed to a method for producing a grid-like beam collimator, the method comprising:

printing a suspension, including a binder and metal particles, in several stacked layers to build a layer stack with a grid structure including a number of crossing webs, and including removal of the binder from the layer stack, the printing including applying a curable liquid stiffening material at least on a surface of the grid structure, and curing the liquid stiffening material after the applying.

Furthermore, at least one embodiment of the invention relates to a grid-like beam collimator comprising a grid structure with a number of crossing webs, the grid structure be made of metal particles and a cured stiffening material applied to the surface of the grid structure or present in the grid structure.

Furthermore, at least one embodiment of the invention relates to a radiation detector comprising a grid-like beam collimator of at least one embodiment.

Furthermore, at least one embodiment of the invention relates to a medical imaging system, especially a CT system, comprising a radiation detector of at least one embodiment.

BRIEF DESCRIPTION OF THE DRAWINGS

Additional advantages and features of the invention become evident from the embodiment discussed below and from the figures. The figures show.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the inventive method allows the production of a grid-like beam collimator by printing a suspension or paste through a sieve for building a layer stack without any shrinking problems due to a sintering heat treatment. According to at least one embodiment of the inventive method, the grid structure is printed in the first step. Afterwards the binder is removed from the layer stack, which binder is part of the suspension. Furthermore, a liquid stiffening substance or a stiffening material is applied to the grid structure, at least on the surface of the grid structure for covering the same. The application can be done in separate ways to which reference is made afterwards. The stiffening substance or a stiffening material is curable, as it can be transferred from its liquid state, which has it while it is applied, to a solidified state after curing. In this solidified state the stiffening substance or a stiffening material stiffens and stables the layer stack respectively the grid structure, so that it is hard enough to be further processed.

The grid structure is printed using a suspension including a binder and metal particles. A non-exclusive list of possible binders include for example Hydroxypropyl cellulose, Methyl hydroxyethyl cellulose, Ethyl cellulose (EC), PVB (Polyvinyl butyral), PVP (Polyvinylpyrrolidon), PVA (Polyvinyl alcohol), PEG (Polyethylen glycol) or a combination thereof.

In addition to a binder and metal particles, the suspension can also comprise further components to influence rheology and printing characteristics of the suspension. The suspension can, for example, further comprise one or more thickening agents, e.g. RHEOBYK-H 3300 VF (provided by BYK-Chemie GmbH); plasticizers, e.g. Glycerol, Polypropylene glycol, or Dibutyl phthalate; and/or dispersing agents, e.g. trioxadecanoic acid, Dynol, or Polyvinyl pyrrolidone (PVP).

In EP 1 342 760 A1, for example, a suspension for screen printing techniques is described using PVP as binder. Thomas Maeder et al. "Formulation and processing of screen-printing vehicles for sacrificial layers on thick-film and LTCC substrates" (Proceedings, XXXII international conference of IMAPS Poland Chapter, 2008) discloses screen-printing vehicles for thick-film and LTCC structuration techniques using, for example, PVA or EC as binder.

At least one embodiment of the inventive method does not need a sintering step comprising the heating of the printed grid structure to a very high temperature for melting or softening the metal particles made for example from tungsten or molybdenum having very high melting temperatures.

Therefore, a shrinking of the grid or web structure will not occur, the final structure still has the same geometry and, referred to its webs, the same web width and height also after the final curing step. Webs with a plane and smooth surface can be realized as they maintain their geometry and dimensions. A very accurate and process stable manufacturing is possible with at least one embodiment of the inventive method.

The removal of the binder can be realized by a soft heat treatment of the printed grid structure for vaporizing the binder material or for decomposing it. The metal particles are still sticking together even when the binder is at least partially removed, as the metal particles still stick together at the areas where they are in contact with each other. Also a debindering by using a solvent is possible.

The inventive method allows the production of a grid-like beam collimator without any heat treatment for sintering the web structure so that the danger of a temperature induced shrinking is completely avoided. A sintering step comprises the heating of the printed grid structure to a very high temperature for melting or softening the metal particles made for example from tungsten or molybdenum having very high melting temperatures.

A soft heat treatment comprises using lower temperatures for heating the structure than temperatures used in a sintering heat treatment. A soft heat treatment comprises preferably heating the grid structure to less than 1000° C., more preferably less than 700° C. A soft heat treatment can, for example, comprise heating the printed grid structure up to a temperature of 600° C. or 700° C. In a particularly preferred embodiment of the inventive method the grid structure is heated to at least 250° C. and less than 650° C. In another particular embodiments, the grid structure is heated up to at least 300° C. For example, the grid structure is heated up to 300° C. in steps of 5K/min, followed by heating the structure up to 600° C. in steps of 3K/min and followed by keeping the grid structure at 600° C. for a certain period of time, e.g. 20 min to 300 min. The binder can thereby be removed as far as possible, while it is not harmful when a residual amount of binder remains in the structure, as long as pores or openings are created in the webs due to the removal of the binder.

If, according to another embodiment of the invention, a solvent is used to remove the binder, the solvent is chosen in accordance with the used binder. Preferably volatile solvents, e.g. Aceton, are used for debindering.

The stiffening material is applied at least on the surface of the grid structure, so that it bewets the metal particles at the surface or close to the surface, and firmly bonds them together after curing. Preferably the stiffening material is infiltrated into the grid structure. The stiffening material is not only applied at the surface of the grid structure, but is also infiltrated into the grid structure to a respective depth of preferably at least 10%, especially to at least 20% of the thickness of the respective webs of the grid structure. As the stiffening material is infiltrated from all sides of the respective web, the respective web is stiffened to a certain depth, to where the stiffening material is infiltrated. It is certainly possible to completely infiltrate the stiffening material, so that it is present in the whole web and therefore stiffens the whole web through and through.

The infiltration can be performed at room temperature or at an elevated temperature, it is also possible to apply an elevated pressure or a vacuum alternatively or additionally. Any of these devices/methods which is helpful to enhance the infiltration process respectively the infiltration speed can be used.

Preferably a temperature of or between 20° C. to 200° C. is chosen for infiltration. Heating the grid structure to elevated temperatures above room temperature can thereby support or accelerate infiltration.

According to an embodiment of the invention the infiltration can be supported using pressure assisted infiltration. Pressure assisted infiltration can be based on applying an elevated pressure above prevailing air pressure or based on vacuum applying a pressure below prevailing air pressure or a combination of both. To support infiltration preferably an effective difference in pressure of or between 100 mbar to 1100 mbar, more preferably of or between 700 mbar to 1050 mbar, is chosen with respect to the selected infiltration medium. For example, a vacuum based pressure assisted infiltration method can be used applying a pressure between 1 mbar and 950 mbar with respect to the selected infiltration medium.

The stiffening material is preferably a polymer which is in a liquid state while being applied or infiltrated. The term "polymer" refers to any organic material which can be cured, it also covers any kind of glue or adhesive, as long as it is liquid at the application or infiltration temperature and can be cured afterwards. The polymer stiffening material can comprise a further chemical binder, e.g. based on sodium silicate, potassium silicate or lithium silicate. Commercially available chemical binders comprise, for example, Lithopix P1 (Zschimmer & Schwarz) or similar, as well as, for example, Lithosol 1530 (Zschimmer & Schwarz) or similar. The stiffening material can also comprise an epoxy, a water based sealer (e.g. Nano-Seal 180W provided by Jeln Imprägnierung GmbH or similar), a solvent based sealer (e.g. Nano-Seal 120R provided by Jeln Imprägnierung GmbH or similar) or silicon resins (e.g. Silres H62c provided by Wacker Chemie AG or similar), wherein this list is a non-exclusive list and further materials, not explicitly named but with the above described characteristics, shall not be excluded. The stiffening material can be further thinned with water or a solvent for application, e.g. when using a chemical binder, or may be directly applied, e.g. when using a water-based sealer.

The curing of the stiffening substance or a stiffening material can be realized by separate or different methods, while the respective method to be used depends on the properties of the stiffening material respectively of the polymer used. It is possible to cure the stiffening substance or a stiffening material, especially the polymer, by additionally applying or infiltrating a curing device, like a curing or crosslinking agent, which reacts with the infiltrated stiffening material/substance respectively polymer. Besides performing a chemical curing, it is also possible to perform the curing by irradiating UV light onto the printed web structure, when the stiffening material respectively polymer is a light curable material.

The curing can also be performed by heat curing wherein the layer stack is heated to an appropriate curing temperature, which is much lower than the melting temperature of the metal particles. Finally, the curing can also be performed by dry curing, wherein the applied or infiltrated stiffening material is dried at room temperature.

Alternatively to using a polymer as a stiffening material it is possible to use a metal as a stiffening material, for example a metal which has a relatively low melting temperature compared to the melting temperature of the metal particles. As such a metal for example tin, silver, copper, nickel or an alloy of at least two of these metals can be used. It is advantageous to use a metal with a very low melting temperature to avoid that the web structure is heated too much due to the application of the metal.

In case that the stiffening materials are metal the curing is preferably performed by cooling the layer stack.

As already mentioned, there are several different methods for applying the stiffening material on the layer stack. According to a first alternative the stiffening material is sprayed or dispensed on the layer stack. The stiffening material can for example be sprayed directly on the web structure by using a respective spraying device. It can also be otherwise dispensed on the layer stack, for example by pouring it on the layer stack or the like.

Alternatively to these methods it is possible to apply the stiffening material by immersing the layer stack into the liquid stiffening substance or material. According to this embodiment, the layer stack is immersed into a kind of bath containing the liquid stiffening device or a stiffening material, it remains into this bath as long as it is needed for the infiltration and reaching the infiltration depth if necessary, whereupon it is removed from the bath. Afterwards, the curing takes place.

A third alternative for applying the stiffening material is the printing of the stiffening material on the layer stack, preferably by serigraphy, i.e. by printing the liquid stiffening material through a sieve. When the stiffening material is liquid enough it is possible that the stiffening material bewets all sides of the webs, so that the web structure is completely covered at the surface and can therefore be stiffened in all areas.

Finally the application can be performed by attaching a foil to the layer stack and heat the foil above its melting temperature. The foil is made of the stiffening material and is melted after attaching it to the layer stack by simply heating the foil. Especially when the foil is a polymer foil, the heating temperature is very low to get it melted, so that it bewets the webs of the grid structure on all surfaces.

At least one embodiment of the inventive method allows the production of a grid-like beam collimator without any heat treatment for sintering the web structure. The danger of a temperature induced shrinking is completely avoided, allowing the production of collimators with a very high precision regarding the geometry and the dimensions. Due to this during the printing no measure need to be taken in view of any changes in the dimensions due to the shrinking, so that more collimators or grid structure can be printed on the same surface as compared to the sintering method according to the prior art.

It is also possible to print the web structure with different web thickness, so that especially thinner webs or walls are possible. It is possible that the outer webs or walls of the printed structure have a lower thickness, so that several printed structures can be placed next to each other with the outer webs or walls contacting each other, so that the effective thickness of these double-walled webs is the same as of the webs in the inner part of the respective grid structures.

Also the printing of slanting webs is possible, so that the webs or the collimator can be focused to an x-ray focus.

The metal particles are non-reactive arranged in the stiffening material or matrix. Also mixtures or alloys of different metal particles can be used.

Furthermore, at least one embodiment of the invention relates to a grid-like beam collimator comprising a grid structure with a number of crossing webs, the grid structure be made of metal particles and a cured stiffening material applied to the surface of the grid structure or present in the grid structure.

The stiffening material can be applied only onto the surface by any of the above mentioned devices/methods, so that it is present only on the surface and in a thin boundary layer. As an alternative the stiffening material can be present in the respective webs to a certain depth. Also this can be performed by any of the above mentioned devices/materials/substances/methods. In case the stiffening material is applied, i.e. present within the webs it is advantageous to have it introduced to a depth to at least 10%, preferably to at least 20% of the thickness of the respective webs of the grid structure.

The stiffening substance is preferably a polymer, alternatively a metal can be used.

Preferably the webs define passage channels in the shape of truncated pyramids, with the longitudinal axes of the channels being aligned to a common focus. The webs, which are preferably remarkably thinner than the channels to avoid shading of active pixels of the radiation active matrix of the radiation detector and to have a high dose application, are slanted or tapered, so that they confine openings or channels of frustum shape, which are aligned with their longitudinal axes to a common focus. This truncated pyramid geometry can be realized with very high precision, as no shrinking occurs according to the inventive way of manufacturing the web structure. During the printing process the cross section varying with the height of the webs respectively the channels in the shape of the truncated pyramids can be produced by replacing the printing screen used at least once or preferably several times with a successively changing printing geometry. In this embodiment the thickness of the webs varies over the height with the webs becoming thinner in the direction to the common focus. This also allows aligning the channels to a common focus.

The collimator can have an overall shape of a truncated pyramid with parallel upper and lower surfaces and slanted sides. Also the webs at the edge of the collimator can be slanted. This enables arranging several smaller collimators in a row for building a polygonal ring collimator for arranging in the gantry of a CT system. Certainly such a truncated collimator can also be used as a single collimator for example in a X-ray application comprising a movable C-bow or the like. Alternatively it can have a cuboid shape with parallel and vertical edge webs, which embodiment is preferably for single use of the collimator. This collimator having thicker edge webs is advantageous as it shows a higher stability when finally being hardened.

In an alternative the printed collimator can also be printed in a bent form or can be mechanically bent after printing or producing smaller collimators which can be arranged in a row for building a ring shaped collimator for a gantry of a CT system. Due to the large radius from the collimator ring to the central focus the mechanical deformation is small allowing to maintain the focus. For bending the printed but not yet hardened collimator one or more cylindrical drums can be used.

At least one embodiment of the invention also refers to a radiation detector, especially a X-ray detector, comprising a grid-like beam collimator produced according to at least one embodiment of the inventive method or as depicted above.

Finally at least one embodiment of the invention refers to a medical imaging system, especially a CT-system comprising a radiation detector as depicted above.

Figure 1:
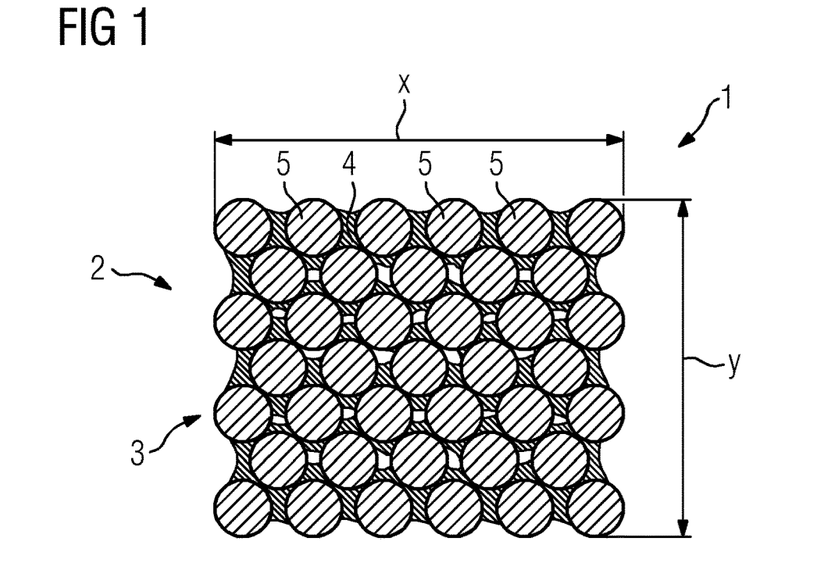
FIG. 1 shows a principle sketch of a grid-like beam collimator in a partial view as a cross-sectional view through the web of the grid structure after printing.

FIG. 1 shows an embodiment of inventive grid-like beam collimator 1 as a principle sketch. It comprises a web or grid structure 2 comprising several crossing webs 3, one of which is shown in a cross-sectional view in FIG. 1. The web or grid structure 2 is built by printing of a suspension or paste comprising a liquid or pasty binder 4 and metal particles 5, for example made of tungsten or molybdenum. This suspension or paste is printed through a sieve (serigraphy), several separate layers are printed above each other for building a layer stack. The printing is performed until the web or grid structure 2 has its final shape, geometry and dimension. As shown in FIG. 1 each web has a width x and a height y.

The binder 4 connects the respective metal particles 5, so that the printed web or grid structure 2 is somehow stable and maintains its shape. Nevertheless, the printed layer stack can comprise certain gaps or fissures between the metal particles 5.

After the printing the web or grid structure 2 is for example heat treated in order to remove the liquid or pasty binder 4 from the printed web or grid structure 2.

Figure 2:
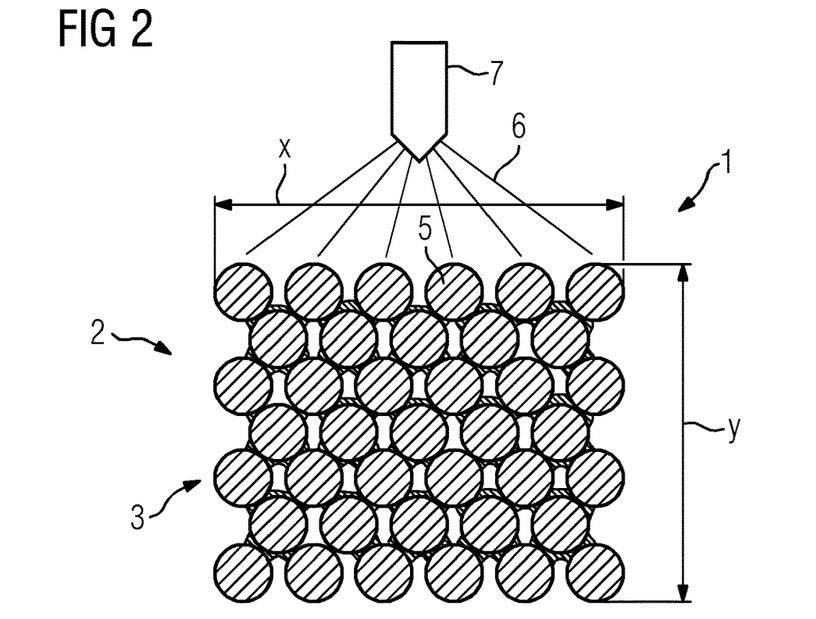
FIG. 2 shows the web of FIG. 1 after removal of the binder and while applying the liquid stiffening material.

The web of FIG. 1 after removal of the liquid or pasty binder 4 is shown in FIG. 2. The metal particles 5 still stick together, although some or most of the liquid or pasty binder 4 is removed. The web or grid structure 2 maintains its dimensions x and y. Nevertheless the web or grid structure 2 shows many gaps of fissures, what makes it possible to infiltrate a liquid stiffening substance 6, which is for example applied by spraying or dispensing this liquid stiffening substance 6 by way of a spraying device 7. This liquid stiffening substance 6 is preferably a polymer, which has a low melting temperature, so that the printed web or grid structure 2 is not strongly heated while the liquid stiffening material 6 is applied.

The liquid stiffening material 6 may be applied only to the surface of the web or grid structure 2 or respectively the crossing webs 3, therefore solely bewettening the outer metal particles 5, what will be enough for stiffening the overall web or grid structure 2 when the liquid stiffening material 6 is cured afterwards. Preferably the liquid stiffening material 6 is infiltrated into the respective web or grid structure 2 respectively the crossing webs 3, so that it flows into the respective crossing web 3 to a certain depth, preferably it is present all over the respective crossing web 3.

Figure 3:
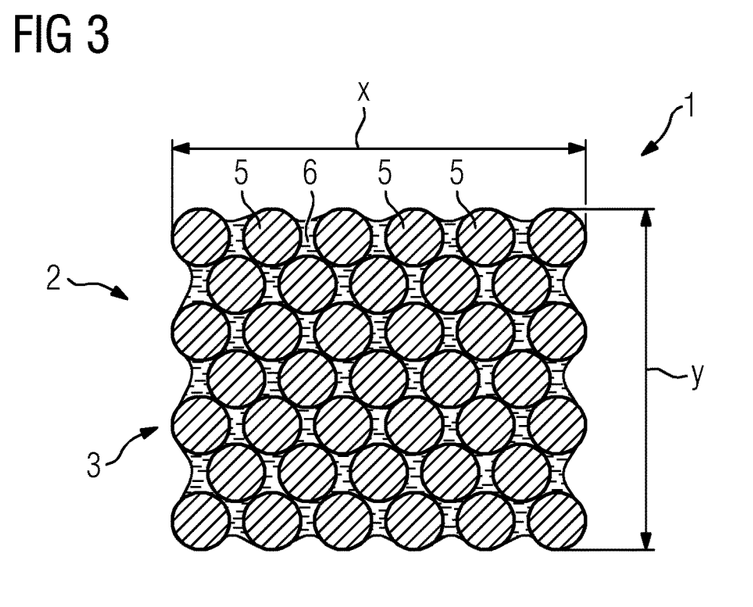
FIG. 3 shows the web of FIG. 2 after infiltrating the liquid stiffening material into the web.

FIG. 3 shows the crossing web 3 of FIG. 2 with the liquid stiffening material 6 respectively the polymer infiltrated into the whole crossing web 3, which still has its printed dimensions x and y. As can be seen all metal particles 5 are bewetted or contacted by the liquid stiffening material 6.

Figure 4:
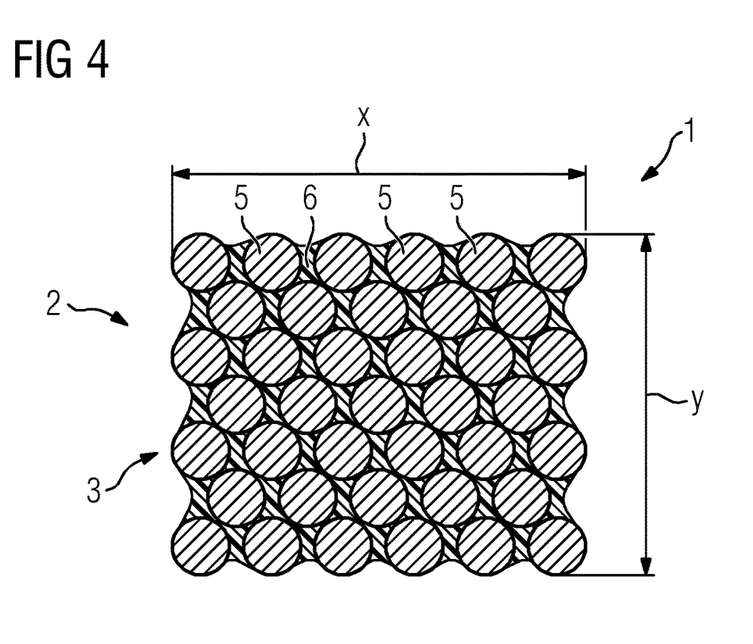
FIG. 4 shows the web of FIG. 3 after curing the infiltrated liquid stiffening material.

In a final step the liquid stiffening material 6 is cured to be solidified. This curing or solidification can be performed by various methods. It is possible to simply slightly heat the web or grid structure 2 for hardening the liquid stiffening material 6. It is also possible to apply UV light, when the liquid stiffening material 6 is light curable.

Whatever method is used, as a result the liquid stiffening material 6 is solidified and firmly stiffens and stables respectively contacts the metal particles 5. The whole web or grid structure 2 is very stable and can be handled respectively further processed, while maintaining its dimensions without the danger of shrinking.

Figure 5:
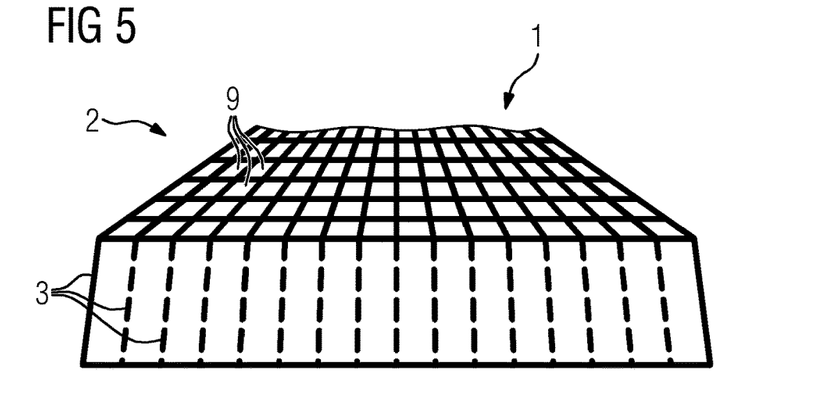
FIG. 5 shows a principal perspective sketch of an embodiment of an inventive grid-like beam collimator with webs aligned to a common focus.

FIG. 5 shows a principal illustration of an embodiment of an inventive collimator 1. It comprises a grid-like web structure 2 having plane upper and lower sides and with crossing webs 3 (which are shown on the front side by the dashed lines), which are aligned to a common focus, as they are more and more slanted beginning from the center to the sides. The thickness of the crossing webs 3 remain the same over their height. As the crossing webs 3 define passage channels 9 also these channels are focused, their longitudinal axes are aligned to the common focus. The collimator 1 has the overall shape of a truncated pyramid. This geometry can be produced with the printing process, whereby the printing screen needs to be changed once or several times due to the varying geometry over the height of the web structure 2.

Figure 6:
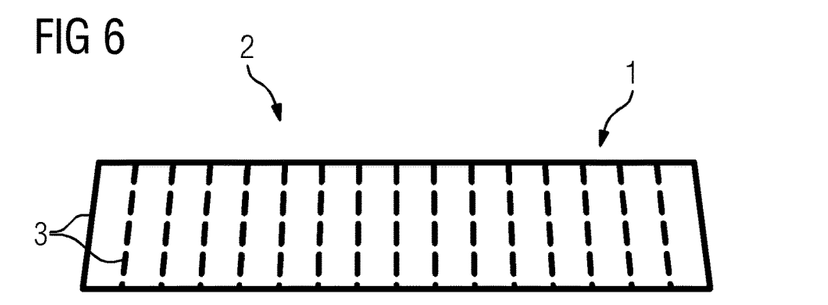
FIG. 6 shows a principal sketch of an embodiment of an inventive grid-like beam collimator with webs varying in their thickness and aligned to a common focus.

FIG. 6 shows a side view of a collimator 1 of another inventive embodiment, which has also plane upper and lower sides. The web structure 2 with the crossing webs 3 is also aligned to a common focus, but the thickness of the crossing webs 3 varies with the height of the webs. The crossing webs 3 become thinner in the direction to the focus the higher they are. Also this web geometry can be produced with the printing process with changing the printing screen.

Figure 7:
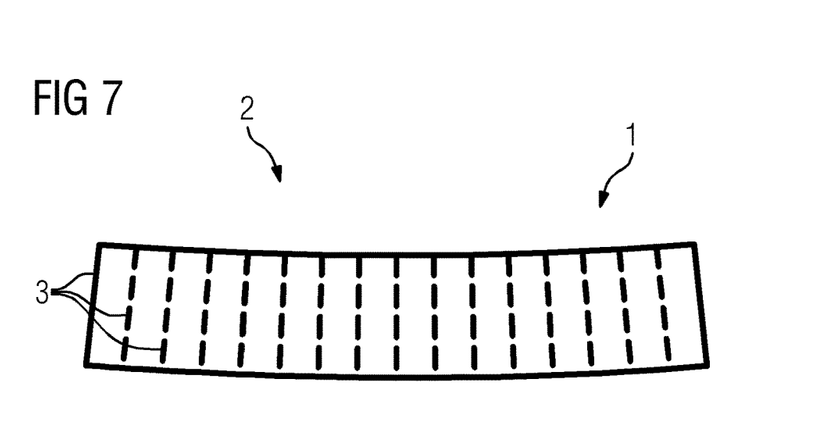
FIG. 7 shows a principal sketch of an embodiment of an inventive grid-like beam collimator being bent.

FIG. 7 finally shows a collimator 1 with a web structure 2 which is bent for aligning the web structure 2 respectively the crossing webs 3 to a common focus. This bending can either be realized during the printing process, meaning that the web structure 2 is printed in the bent form. In an alternative the web structure 2 is printed with parallel upper and lower surfaces and is afterwards mechanically bent.

Figure 8:
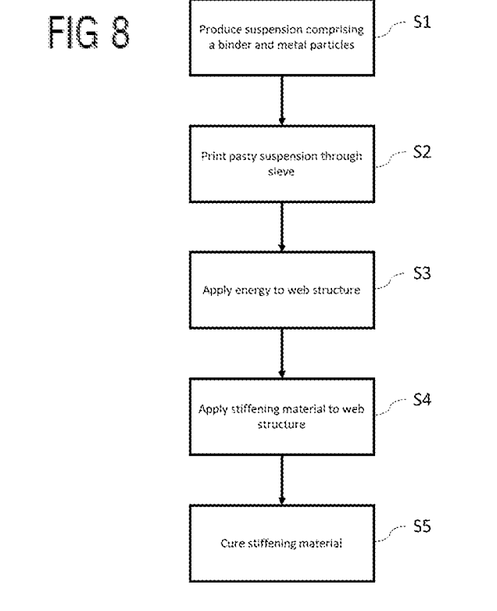
FIG. 8 shows a flow chart explaining the steps of an embodiment of the inventive method.

FIG. 8 shows a flow chart explaining an embodiment of the inventive method. In step S1 a suspension comprising a binder and metal particles is produced. The metal particles may be of molybdenum or tungsten for example. The viscosity of the suspension is chosen for a sieve printing method.

The pasty suspension is then, see step S2, printed through a sieve defining a web structure to produce a printed web structure respectively a collimator. The structure is built by printing several printed layers above each other for building a layer stack. If a focused collimator shall be produced the sieve is frequently changed so that the printed webs become slanted. Thus the channels or openings defined by the slanted webs will have a frustum or truncated pyramid form with the longitudinal axes of the channels being all aligned to a common focus. As each channel is bounded by four webs it has a square cross section. It is also possible to vary the web thickness over the structure so that regions with smaller webs and regions with larger webs can be built.

After printing of the web structure energy is applied to the web structure to remove the binder, see step S3. The energy can be applied by heating the web structure or by applying a solvent to the web structure. The binder is removed as far as possible, while it is not harmful when a residual amount of binder remains in the structure, as long as pores or openings are created in the webs due to the removal of the binder.

When the binder is removed a stiffening material is applied in step S4. The application can be done in several ways. It can be sprayed or dispensed on the layer stack or is applied by immersing the layer stack into the liquid stiffening material. Alternatively it can be printed on the layer stack, or it can be attached as a foil to the layer stack and heated above its melting temperature. The stiffening material can be applied only to the surface of the webs or it can be moved into the webs until a certain depth. The infiltration into the webs can be made by room temperature when the webs show a certain absorptive capacity or can be driven be heating the web structure or by applying a higher pressure. The stiffening material is preferably moved to a depth of at least 20% of the web thickness.

Finally, see step S5, the stiffening material is cured to harden the webs. This hardening can be done for example by applying a curing device or by applying UV light or by heating the structure to a curing temperature or at room temperature in case of using a polymer stiffening material. The needed method is chosen depending on the properties of the stiffening material. When metal is used as a stiffening material the hardening is performed simply by cooling the structure.

Figure 9:
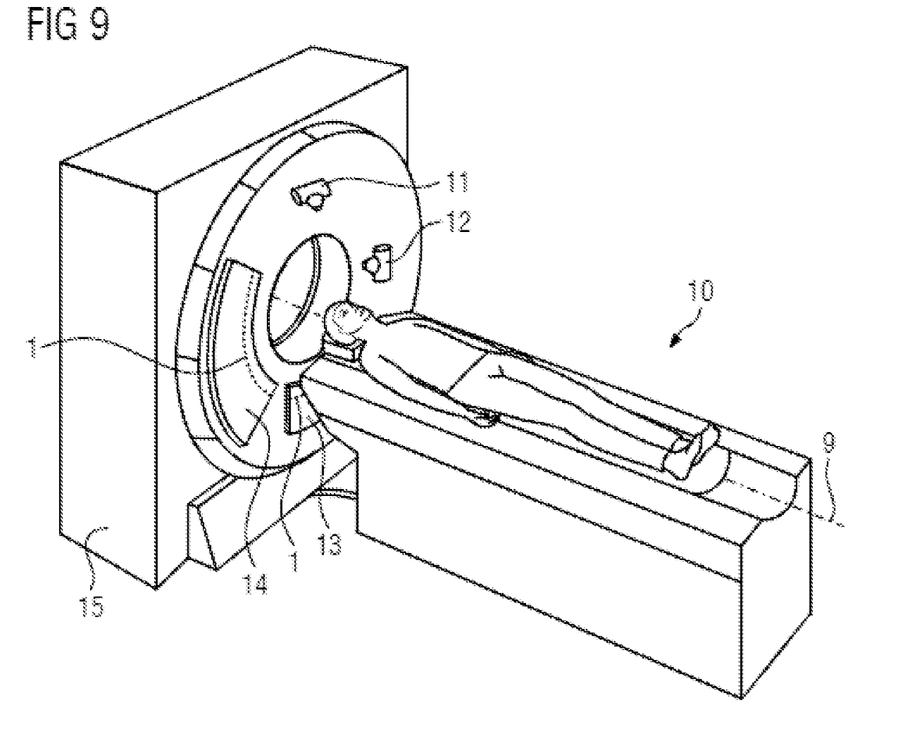
FIG. 9 shows a medical imaging system in form of a CT system.

FIG. 9 shows a principal sketch of a medical imaging device in form of a CT system 10. The CT system 10 is a dual source system comprising two radiation sources 11 and 12, e.g. X-ray sources, which are offset by an angle of 90°. If further comprises two radiation detectors 13 and 14, with the two radiation detectors 13 and 14 being also offset by an angle of 90° and arranged opposite to the radiation sources 11 and 12. If the CT system 10 is not a dual source systems only one radiation source with an opposite radiation detector is provided. The source-detector pairs are arranged on a gantry in a gantry housing 15.

Both radiation detectors 13 and 14 each have one or more grid-like beam collimators 1 with one or more scattered radiation grids. The scattered radiation grids are produced as described above, they can be modular in structure and bring about a reduction of scattered radiation in both the phi direction and the z direction. The z direction here is considered to be the coordinate axis and phi is considered to be the rotational direction of the gantry.

Although the present invention has been described in detail with reference to the preferred embodiment, the present invention is not limited by the disclosed examples from which the skilled person is able to derive other variations without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for producing a grid-like beam collimator, the method comprising:
   printing a suspension comprising a binder and metal particles in several stacked layers to build a layer stack with a grid structure including a number of crossing webs,
   the printing comprising:
   removing the binder from the layer stack,
   applying a curable liquid stiffening material at least on a surface of the grid structure, and
   curing the curable liquid stiffening material after the applying the curable liquid stiffening material.

2. The method of claim 1, wherein the step of applying the curable liquid stiffening material at least on the surface of the grid structure comprises infiltrating the curable liquid stiffening material into the grid structure.

3. The method of claim 2, wherein the step of infiltrating the curable liquid stiffening material into the grid structure comprises infiltrating the curable liquid stiffening material into the grid structure to a depth of at least 10% of a thickness of respective crossing webs of the number of crossing webs of the grid structure.

4. The method of claim 3, wherein the step of infiltrating the curable liquid stiffening material into the grid structure comprises infiltrating the curable liquid stiffening material into the grid structure at at least one of a room temperature, an elevated temperature, an elevated pressure, and under a vacuum.

5. The method of claim 2, wherein the step of infiltrating the curable liquid stiffening material into the grid structure comprises infiltrating the curable liquid stiffening material into the grid structure at at least one of a room temperature, an elevated temperature, an elevated pressure, and under a vacuum.

6. The method of claim 2, wherein the step of infiltrating the curable liquid stiffening material into the grid structure comprises infiltrating the curable liquid stiffening material into the grid structure to a depth of at least 20% of a thickness of respective crossing webs of the number of crossing webs of the grid structure.

7. The method of claim 2 wherein the step of applying the curable liquid stiffening material at least on the surface of the grid structure comprises applying a polymer as the curable liquid stiffening material, and wherein the step of curing the curable liquid stiffening material comprises curing the polymer by applying or infiltrating the polymer via at least one of a curing device, UV light, heating the layer stack, or drying at a room temperature.

8. The method of claim 2, wherein the step of applying the curable liquid stiffening material at least on the surface of the grid structure comprises applying a metal as the curable liquid stiffening material, and wherein the step of curing the curable liquid stiffening material comprises curing the metal by cooling the layer stack.

9. The method of claim 1, wherein the step of applying the curable liquid stiffening material at least on the surface of the grid structure comprises applying a polymer as the curable liquid stiffening material, and wherein the step of curing the curable liquid stiffening material comprises curing the polymer by applying or infiltrating the polymer via at least one of a curing device, UV light, heating the layer stack, or drying at a room temperature.

10. The method of claim 1, wherein the step of applying the curable liquid stiffening material at least on the surface of the grid structure comprises applying a metal as the curable liquid stiffening material, and wherein the step of curing the curable liquid stiffening material comprises curing the metal by cooling the layer stack.

11. The method of claim 10, wherein the metal is selected from the group consisting of tin, silver, copper, nickel, and an alloy of at least two of tin, silver, copper, and nickel.

12. The method of claim 1, wherein the step of applying the curable liquid stiffening material at least on the surface of the grid structure comprises:
   spraying or dispensing the curable liquid stiffening material on the layer stack,
   immersing the layer stack into the curable liquid stiffening material,
   printing the liquid stiffening material on the layer stack, or
   attaching the liquid stiffening material as a foil to the layer stack and heated above a melting temperature of the curable liquid stiffening material.

13. The method of claim 1, wherein the step of removing the binder from the layer stack comprises removing the binder by a heat treatment or by a solvent.

14. A grid-like beam collimator, comprising:
a grid structure comprising:
a number of crossing webs,
metal particles, and
a cured stiffening material,
wherein the cured stiffening material is present on a surface of the grid structure or present in the grid structure, and
wherein the grid structure has a shape of a truncated pyramid.

15. The grid-like beam collimator of claim 14, wherein the cured stiffening material is present to a depth of at least 10% of a thickness of the number of crossing webs of the grid structure.

16. The grid-like beam collimator of claim 15, wherein the cured stiffening material is present to a depth of at least 20% of a thickness of the number of crossing webs of the grid structure.

17. The grid-like beam collimator of claim 15, wherein the cured stiffening material comprises a polymer or a metal.

18. The grid-like beam collimator of claim 14, wherein the cured stiffening material comprises a polymer or a metal.

19. The grid-like beam collimator of claim 14, wherein the number of crossing webs define passage channels, with longitudinal axes of the passage channels being aligned to a common focus.

20. A radiation detector, comprising:
a radiation active pixel matrix; and
a grid-like beam collimator of claim 14,
wherein the number of crossing webs define passage channels in tea shape of truncated pyramids with longitudinal axes of the passage channels aligned to a common focus, and
wherein the number of crossing webs are thinner than the passage channels and are slanted and/or tapered.

21. A CT system comprising;
a radiation detector comprising a grid-like beam collimator of claim 14;
at least one radiation source opposite to the radiation detector; and
a gantry housing comprising a gantry,
wherein the at least one radiation source and the radiation detector are arranged on the gantry in the gantry housing.

* * * * *